(12) United States Patent
Noguchi et al.

(10) Patent No.: US 8,043,505 B2
(45) Date of Patent: Oct. 25, 2011

(54) TREATMENT EQUIPMENT OF ORGANIC WASTE AND TREATMENT METHOD

(75) Inventors: Akiteru Noguchi, Kanagawa (JP); Koichi Doi, Kanagawa (JP); Katsuhiro Tsubai, Kanagawa (JP)

(73) Assignee: EnerTech Environmental, Inc., Atlanta, GA (US)

( * ) Notice: Subject to any disclaimer, the term of this patent is extended or adjusted under 35 U.S.C. 154(b) by 280 days.

(21) Appl. No.: 11/919,276

(22) PCT Filed: Mar. 16, 2006

(86) PCT No.: PCT/JP2006/305223
§ 371 (c)(1),
(2), (4) Date: Oct. 24, 2007

(87) PCT Pub. No.: WO2006/117934
PCT Pub. Date: Nov. 9, 2006

(65) Prior Publication Data
US 2009/0032464 A1    Feb. 5, 2009

(51) Int. Cl.
*C07C 4/00* (2006.01)
*C10L 1/04* (2006.01)
*C02F 11/00* (2006.01)
*C02F 1/44* (2006.01)

(52) U.S. Cl. ............... 210/257.2; 210/637; 210/787; 210/360.1; 210/151; 210/512.1; 210/513; 208/424; 208/425; 208/428; 208/429; 208/430; 422/533; 422/600; 422/608; 422/613; 422/614

(58) Field of Classification Search .............. None
See application file for complete search history.

(56) References Cited

U.S. PATENT DOCUMENTS 3,580,193 A    5/1971    Logan et al.
(Continued)

FOREIGN PATENT DOCUMENTS

CN    1396142    2/2003
(Continued)

OTHER PUBLICATIONS

English language translation of Office Action dated Jul. 31, 2009 in corresponding Chinese Application No. 200680014592.6.
(Continued)

*Primary Examiner* — Krishnan S Menon
(74) *Attorney, Agent, or Firm* — Baker & Daniels LLP

(57) ABSTRACT

In treatment equipment of organic waste provided with a high temperature and pressure treatment apparatus to produce a slurried material by conducting the high temperature and high pressure treatment of the organic waste, a dehydration treatment apparatus to recover the dehydrated solid matter by conducting the dehydration treatment of the slurried material and a water treatment apparatus to conduct the purification treatment of a separated liquid separated by the dehydration treatment apparatus, the treatment equipment of organic waste is characterized by having a crusher to crush said organic waste before conducting the high pressure and temperature treatment and providing to said high temperature and pressure treatment apparatus a steam blowing means to blow steam into the organic waste in said high temperature and pressure treatment apparatus, wherein said high temperature and pressure treatment apparatus is formed as a continuous reaction tank to which the organic waste is continuously supplied and to which the steam is blown from the said steam blowing means to cause the reaction while heating, pressurizing and agitating, and wherein said water treatment apparatus is provided with a membrane separation treatment apparatus to conduct the separation treatment via the separation membrane as a condensed liquid of the residual solid matter in the separated liquid.

20 Claims, 2 Drawing Sheets

U.S. PATENT DOCUMENTS

| | | |
|---|---|---|
| 3,729,042 A | 4/1973 | Burnett |
| 3,830,636 A | 8/1974 | Marsh |
| 4,017,421 A | 4/1977 | Othmer |
| 4,038,152 A | 7/1977 | Atkins |
| 4,087,276 A | 5/1978 | Generini |
| 4,128,946 A | 12/1978 | Maffet |
| 4,208,245 A | 6/1980 | Watkins et al. |
| 4,229,296 A | 10/1980 | Wheaton et al. |
| 4,241,722 A | 12/1980 | Dickinson |
| 4,255,129 A | 3/1981 | Reed et al. |
| 4,272,322 A | 6/1981 | Kobayashi |
| 4,284,015 A | 8/1981 | Dickinson |
| 4,290,269 A * | 9/1981 | Hedstrom et al. ............ 60/670 |
| 4,292,953 A | 10/1981 | Dickinson |
| 4,377,066 A | 3/1983 | Dickinson |
| 4,380,960 A | 4/1983 | Dickinson |
| 4,477,257 A | 10/1984 | Koppelmann et al. |
| 4,593,202 A | 6/1986 | Dickinson |
| 4,615,711 A | 10/1986 | Muller |
| 4,618,735 A | 10/1986 | Bridle et al. |
| 4,657,681 A | 4/1987 | Hughes et al. |
| 4,702,745 A | 10/1987 | Kamei et al. |
| 4,714,032 A | 12/1987 | Dickinson |
| 4,721,575 A | 1/1988 | Binning et al. |
| 4,735,729 A | 4/1988 | Dietrich et al. |
| 4,761,893 A | 8/1988 | Glorioso |
| 4,795,568 A | 1/1989 | Chen |
| 4,824,561 A | 4/1989 | Huang et al. |
| 4,829,678 A | 5/1989 | Glorioso |
| 4,852,269 A | 8/1989 | Glorioso |
| 4,860,671 A | 8/1989 | Glorioso |
| 4,869,833 A | 9/1989 | Binning et al. |
| 4,875,905 A | 10/1989 | Somerville et al. |
| 4,898,107 A | 2/1990 | Dickinson |
| 4,909,899 A | 3/1990 | Kiiskila |
| 4,953,478 A | 9/1990 | Glorioso |
| 4,956,926 A | 9/1990 | Glorioso |
| 4,983,296 A | 1/1991 | McMahon et al. |
| 4,983,782 A | 1/1991 | Merz et al. |
| 4,989,344 A | 2/1991 | Glorioso |
| 5,000,099 A | 3/1991 | Dickinson |
| 5,018,456 A | 5/1991 | Williams |
| 5,019,135 A | 5/1991 | Sealock, Jr. et al. |
| 5,050,375 A | 9/1991 | Dickinson |
| 5,057,231 A | 10/1991 | Mueller et al. |
| 5,075,015 A | 12/1991 | Kamke |
| 5,082,571 A | 1/1992 | Beula et al. |
| 5,087,370 A | 2/1992 | Schultheis et al. |
| 5,087,378 A | 2/1992 | Kovacs |
| 5,114,541 A | 5/1992 | Bayer |
| 5,183,577 A | 2/1993 | Lehmann |
| 5,188,739 A | 2/1993 | Khan et al. |
| 5,188,740 A | 2/1993 | Khan |
| 5,188,741 A | 2/1993 | Zang et al. |
| 5,205,906 A | 4/1993 | Grutsch et al. |
| 5,211,723 A | 5/1993 | Khan |
| 5,211,724 A | 5/1993 | Khan et al. |
| 5,217,625 A | 6/1993 | Khan et al. |
| 5,221,480 A | 6/1993 | Schultheis et al. |
| 5,230,211 A | 7/1993 | McMahon et al. |
| 5,230,810 A | 7/1993 | Clark et al. |
| 5,234,468 A | 8/1993 | Khan |
| 5,234,469 A | 8/1993 | Khan et al. |
| 5,234,607 A | 8/1993 | Brandenburg et al. |
| 5,240,619 A | 8/1993 | Copa et al. |
| 5,261,225 A | 11/1993 | Dickinson |
| 5,264,009 A | 11/1993 | Khan |
| 5,266,085 A | 11/1993 | McMahon et al. |
| 5,273,556 A | 12/1993 | McMahon et al. |
| 5,280,701 A | 1/1994 | Tolman |
| 5,288,413 A | 2/1994 | Chu |
| 5,292,429 A | 3/1994 | DesOrmeaux |
| 5,292,442 A | 3/1994 | Khan et al. |
| 5,337,496 A | 8/1994 | Glorioso |
| 5,339,621 A | 8/1994 | Tolman |
| 5,356,540 A | 10/1994 | Khan et al. |
| 5,370,715 A | 12/1994 | Kortzeborn et al. |
| 5,389,259 A | 2/1995 | Berrigan, Jr. |
| 5,389,264 A | 2/1995 | Lehmann et al. |
| 5,485,728 A | 1/1996 | Dickinson |
| 5,500,044 A | 3/1996 | Meade et al. |
| 5,582,793 A | 12/1996 | Glazer et al. |
| 5,630,854 A | 5/1997 | Sealock, Jr. et al. |
| 5,641,413 A | 6/1997 | Momont et al. |
| 5,707,417 A | 1/1998 | Yokoyama et al. |
| 5,711,768 A | 1/1998 | Schulz |
| 5,797,972 A | 8/1998 | Schulz |
| 5,888,256 A | 3/1999 | Morrison |
| 5,888,307 A | 3/1999 | Solheim |
| 5,888,453 A | 3/1999 | Luker |
| 5,975,439 A | 11/1999 | Chieffalo et al. |
| 6,029,588 A | 2/2000 | Baudhuin |
| 6,063,147 A | 5/2000 | Winter et al. |
| 6,096,283 A | 8/2000 | Cooper et al. |
| 6,103,191 A | 8/2000 | Luker |
| 6,143,176 A | 11/2000 | Nagamatsu et al. |
| 6,149,694 A | 11/2000 | Redden, Jr. et al. |
| 6,197,081 B1 | 3/2001 | Schmidt |
| 6,256,902 B1 | 7/2001 | Flaherty et al. |
| 6,365,047 B1 | 4/2002 | Bischof et al. |
| 6,436,157 B1 | 8/2002 | Winter et al. |
| 6,692,544 B1 | 2/2004 | Grillenzoni |
| 6,740,205 B2 | 5/2004 | Molintas |
| 6,905,600 B2 | 6/2005 | Lee, Jr. |
| 6,913,700 B2 | 7/2005 | Solheim |
| 6,962,561 B2 | 11/2005 | Bruno et al. |
| 6,966,989 B2 | 11/2005 | Hojsgaard et al. |
| 6,978,725 B2 | 12/2005 | Ramharter et al. |
| 7,101,482 B2 | 9/2006 | Chauzy et al. |
| 7,160,442 B2 | 1/2007 | Horng et al. |
| 7,179,379 B2 | 2/2007 | Appel et al. |
| 7,211,229 B2 | 5/2007 | Halli et al. |
| 7,252,691 B2 | 8/2007 | Philipson |
| 7,262,331 B2 | 8/2007 | van de Beld et al. |
| 7,301,060 B2 | 11/2007 | Appel et al. |
| 7,311,834 B2 | 12/2007 | Lee, Jr. |
| 2004/0025715 A1 * | 2/2004 | Bonde et al. ................ 99/485 |
| 2004/0172878 A1 | 9/2004 | Krylowicz et al. |
| 2004/0192980 A1 | 9/2004 | Appel et al. |
| 2004/0192981 A1 | 9/2004 | Appel et al. |
| 2005/0108928 A1 | 5/2005 | Sparks et al. |
| 2005/0113611 A1 | 5/2005 | Adams et al. |
| 2005/0145569 A1 | 7/2005 | Ulmert |
| 2006/0060526 A1 | 3/2006 | Binning et al. |
| 2007/0043246 A1 | 2/2007 | Bridle |
| 2007/0098625 A1 | 5/2007 | Adams et al. |
| 2007/0289205 A1 | 12/2007 | Sparks |
| 2008/0072478 A1 | 3/2008 | Cooper |

FOREIGN PATENT DOCUMENTS

| | | |
|---|---|---|
| EP | 1 717 209 | 11/2006 |
| EP | 1 894 893 | 3/2008 |
| JP | 61252475 A | 11/1986 |
| JP | 08-206691 A | 8/1996 |
| JP | 2004-098003 A | 4/2004 |
| JP | 2006-061861 A | 3/2006 |
| WO | 02/36506 | 5/2002 |
| WO | 02/081379 | 10/2002 |
| WO | 2005/121033 | 12/2005 |
| WO | 2006032282 | 3/2006 |
| WO | 2006053020 | 5/2006 |

OTHER PUBLICATIONS

Neyens, E. et al., "A review of thermal sludge pre-treatment processes to improve dewaterability", Journal of Hazardous Materials, 2003, pp. 51-67.

Weemaes, Marjoleine P.J., et al., "Evaluation of Current Wet Sludge Disintegration Techniques", Centre for Environmental Sanitation, University Ghent, Ghent, Belgium, Jun. 12, 1998.

Walley, Paul, "Optimising Thermal Hydrolysis for Reliable High Digester Solids Loading and Performance", 12th European Biosolids and Organic Resources Conference, 2007.

CH2MHill and Itron, Task 2.2.1 Final Report prepared for the California Energy Commission, "Commonwealth Energy Biogas/PV Mini-Grid Renewal Resources Program, Making Renewables Part of an Affordable and Diverse Electric System in California, Contract No. 500-00-036, Process Selection Report for Wastewater Treatment Plants, Project No. 2.2 Enhanced Energy Recovery Through Optimization of Anaerobic Digestion and Microturbines", Aug. 2003.

Kelly, Harlan G., "Emergy Processes in Biosolids Treatment, 2005", Journal of Environmental Engineering and Science, May 2006.

* cited by examiner

TREATMENT EQUIPMENT OF ORGANIC WASTE AND TREATMENT METHOD

This application is a National Stage of International Application No. PCT/JP2006/305223, filed Mar. 16, 2006, and which claims the benefit of Japanese Patent Application No. 2005-129942, filed Apr. 27, 2005, the disclosures of both applications being incorporated herein by reference.

FIELD OF THE INVENTION

The present invention relates to treatment equipment of organic waste which utilizes the organic waste effectively into a fuel and the like by treating the organic waste under high temperature and high pressure to slurry it and then dehydrating it to recover as a combustible solid raw material, and also relates to a method for treating organic waste.

DESCRIPTION OF PRIOR ART

Heretofore, a method of the incineration or landfill treatment of organic waste has been generally conducted as a method for treating organic waste such as organic sludge, animal and plant remainder or food residue generated from a water treatment apparatus to treat sewage, raw sewage and various industrial wastes. Especially, organic sludge is treated by a method of the incineration or landfill treatment after condensation and dehydration. However, in this method, the bulkiness of the organic waste is large because the moisture-content is as high as 75-82% by weight even after condensation and dehydration of the organic waste. In the case of entrusting the disposal to a professional company or a firm, the cost to take over the wastes to be treated is expensive. Consequently, it is the present situation that a major portion of the cost to the drainage of waste water is largely dominated by this waste collection fee.

In the landfill disposal, the residual operative years of the industrial waste landfill disposal site is getting fewer and the cost to take over is getting higher and higher year by year. In the incineration treatment, the volume of the fuel consumption is large and the energy cost is expensive because the moisture-content is high. Further, in recent years the situation is that the incineration treatment itself is getting more and more difficult due to the problem of dioxin included in the exhaust gas and the incineration ash.

In view of the problem described above, there is provided a method to attempt the effective utilization of the organic sludge as a fuel and the like by treating it under high temperature and pressure, and liquefying or gasifying it. As one of examples, there is a sludge liquefaction apparatus which is provided with a dehydrator to dehydrate the organic sludge, a press fitting device for press-fitting the dehydrated sludge into the following preheater, reactor and cooler in series, the preheater to preheat the dehydrated sludge to be press-fitted by means of a heating medium heated by the cooler of the later step, the reactor to heat the preheated dehydrated sludge with the heating medium and allowing it to react at a temperature of 250° C. or more under a pressure of the vapor pressure or more at this temperature, the cooler to cool the reactant with the heating medium, an atmosphere open type apparatus to open the cooled reactant to atmospheric pressure, a recovering apparatus to recover a combustible liquid in the reactant which is opened to atmosphere and a heating furnace to indirectly heat the heating medium by burning the recovered combustible liquid (for example, see Patent Document 1).

As another example, there is a method which comprises slurrying a lower carbonaceous material such as various dusts and brown coal, conducting the high temperature and pressure treatment to thereby separate oxygen in the carbonaceous material as carbon dioxide and to produce carbonaceous slurry and utilizing the produced gas and the carbonaceous slurry as a fuel (for example, see Patent Document 2).

Further, as another example, there is a method which comprises conducting the strong dehydration treatment of sewage sludge, conducting the high temperature and pressure treatment of the dehydrated sludge (about 150-340° C.) to produce the sewage sludge slurry and flashing off the moisture by flash evaporation, followed by mixing with the adjuvant fuel to produce the quantity of heat controlled slurry fuel (for example, see patent Document 3).

However, in the method or equipment to liquefy the sludge described in Patent Document 1, the liquefaction reaction to produce the oily substance from the sludge takes quite long time because the reaction rate is slow when the reaction is operated under a low temperature and pressure. Therefore, there are problems in that the equipment cost and equipment installation area are increased due to the increase of energy cost and their excessive equipment. Accordingly, the operation is normally performed under high temperature and pressure conditions in order to obtain the efficient reaction rate. However, its temperature and pressure are so high that the energy cost and the equipment cost of the reactor in high pressure design and of the preheater, the heater and the like cause problems.

In the method described in Patent Document 2, since it is not the reaction to produce the oily material, the necessary energy is reduced. In this aspect it is an effective means as a method to attempt the utilization of the waste such as various dusts and sludge into a fuel. However, a large volume of viscosity adjusted water is needed from outside in order to slurry the waste. Especially, sewage sludge is supplied as dehydrated sludge and is highly viscous because the moisture content is 78-82% by weight. This causes problems in that the pressure loss in the feeding pipes and various types of equipment increases, the transportation efficiency is decreased and the overall heat transfer coefficient is reduced. Thus, in order to obtain the sludge having fluidity, the equipment becomes overextended since a further large volume of viscosity-adjusted water is needed.

Further, in the method described in Patent Document 3, the pressure loss in the feeding pipes and various equipment becomes higher, the transportation efficiency is lower and the overall transfer coefficient is lower at the time of heating as compared with the fluid feeding as described above because the dehydrated sludge is further more highly dehydrated under the high temperature and pressure treatment to form the solid matter. Therefore, there are problems in that the energy efficiency is inefficient and the energy cost is costly.

Also, among the types of organic waste to be treated, the organic waste often forms a lump partially or contains the admixture such as woody material, fibrous material and hair. In this case, the higher heating temperature and pressure, and the longer treatment time are necessary when the organic waste is subjected to the high temperature and pressure treatment in the later step as compared to the case in which the lump and the admixture are not included.

[Patent Document 1] JP-B-7-80000
[Patent Document 2] JP-A-9-505878
[Patent Document 3] JP-A-6-246297

DISCLOSURE OF THE INVENTION

Problems to be Solved by the Invention

The present invention has been made in consideration of the situations described above. That is, it is an object of the present invention to provide treatment equipment and a method for treating the organic waste by conducting the high temperature and high pressure treatment to slurry and then dehydrating it to recover as a combustible solid raw material, which is capable of reducing the energy cost and the equipment cost and of preventing the scaling in each component of the equipment and of which the heating temperature, the treatment pressure and the treatment time of the organic sludge in the high temperature and pressure treatment step are approximately equivalent to those of the case in which the organic sludge does not contain the lump of the sludge and the admixture, even when the large lump of the sludge and the admixture are present in the organic waste.

Means to Solve the Problems

According to an exemplary embodiment of the present disclosure, treatment equipment of organic waste is provided with a high temperature and pressure treatment apparatus to produce a slurried material by conducting the high temperature and pressure treatment of the organic waste, a dehydration treatment apparatus to recover a dehydrated solid matter by conducting the dehydration treatment of the slurried material and a water treatment apparatus to conduct the purification treatment of a separated liquid separated by the dehydration treatment apparatus, which is characterized by having a crusher to crush the above organic waste before conducting the high temperature and pressure treatment and providing to the high temperature and high pressure apparatus a steam blowing means to blow steam into the organic wastes in the aforementioned high temperature and pressure apparatus, wherein said high temperature and pressure treatment apparatus is formed as a continuous reaction tank to which the organic waste is continuously supplied and to which the steam is blown from the aforementioned steam blowing means while heating, pressurizing and agitating to cause the reaction, and wherein the water treatment apparatus is provided with a membrane separation treatment apparatus to conduct the separation treatment via the separation membrane as a condensed liquid of the residual solid matter in the separated liquid.

The aforementioned exemplary treatment equipment of organic waste has a preheating tank to preheat the organic waste during the period from after the crushing by the crusher to the supply to the reaction tank, wherein the preheating tank stores a spiral heat exchange agitation tube to agitate the organic waste supplied into the aforementioned preheating tank while preheating with means of heat of the aforementioned heating medium by swirling the heating medium while allowing it to flow into the tube.

The steam blowing means of the aforementioned exemplary treatment equipment of organic waste has a tangent jetting direction nozzle to rotate the organic waste with agitation by jetting the steam to the tangent direction from the jetting port formed at the outer peripheral wall in the organic waste.

The aforementioned exemplary treatment equipment of organic waste has a heat recovery apparatus to recover the quantity of heat of the aforementioned slurried material produced in the aforementioned reaction tank and to cool the slurried material by heat exchange with the heating medium.

The aforementioned exemplary treatment equipment of organic waste is comprised of a first cooler to vacuum and flash the slurried material by the aforementioned recovery apparatus and to heat-exchange the produced steam with the heating medium and a second cooler to heat-exchange the slurried material cooled by the first cooler with the heating medium.

The aforementioned exemplary treatment equipment of organic waste has a slurry storage tank to temporarily store the slurried material and to add water to the slurried material to mix it with agitation.

The aforementioned exemplary treatment equipment of organic waste has a methane fermentation apparatus to ferment an organic matter in the aforementioned separation liquid to thereby produce a methane-containing gas.

According to another exemplary embodiment of the present disclosure, a method is provided for treating organic waste comprising a high temperature and pressure treatment step of conducting the high temperature and pressure treatment of the organic waste to produce a slurried material, a dehydration treatment step of conducting the dehydration treatment of the slurried material produced in the aforementioned high temperature and pressure treatment step to recover a dehydrated solid matter and a water treatment step of conducting the purification treatment of the separated liquid separated in the aforementioned dehydration treatment step, which is characterized by having a crushing step to crush the organic waste before the high temperature and pressure treatment, wherein the high temperature and pressure treatment step is a continuous reaction step to blow steam into the organic waste continuously supplied to the reaction tank while agitating and to conduct the reaction at a temperature of 150-250° C. and a pressure of the steam pressure or more at said temperature for 5-120 minutes and wherein the aforementioned water treatment step includes a membrane separation treatment step to membrane-separate the residual solid matter in the separated liquid as a concentrated liquid.

In the aforementioned exemplary method for treating organic waste, the organic waste is crushed to a size of 5 mm or less.

The aforementioned exemplary method for treating organic waste includes a preheating step to continuously preheat the organic waste in a preheating tank between the aforementioned crushing step and the continuous reaction step, wherein the preheating tank stores a spiral heat exchange agitation tube therein to agitate the organic waste supplied into the aforementioned preheating tank while preheating with heat of the aforementioned heating medium by swirling the heating medium while allowing it to flow into the tube.

In the aforementioned exemplary method for treating organic waste, the reaction tank is equipped with a tangent direction jetting nozzle to jet the steam to the tangent direction from the jetting port formed on the outer peripheral wall and the organic waste in the reaction tank is rotated with agitation while heating by jetting the steam from the jetting port.

The aforementioned exemplary method for treating organic waste comprises adding water to the slurried material to mix with agitation and eluting a water soluble inorganic salt content such as a phosphorus content and a chlorine content in the slurried material.

The aforementioned exemplary method for treating organic waste produces a methane-containing gas by conducting the methane fermentation of the organic matter in the separated liquid.

Effects of the Invention

The simplification of the systemic constitution and the reduction of the equipment cost can be attempted by eliminating a heater for organic waste which was conventionally needed during the high temperature and pressure treatment in the high temperature and pressure treatment apparatus. The heating temperature, treatment pressure and treatment time of the organic sludge in the high temperature and pressure treatment step can be approximately equivalent to those of the case in which the organic sludge does not contain the large lump of the sludge and the admixture even when the large lump of the sludge and the admixture are present in the organic waste because the organic waste is crushed by the crusher before the high temperature and pressure treatment. Further, the reaction efficiency by the uniform heating and uniform agitation of sludge in the reaction tank can be attained since the heating, pressurization and agitation are conducted by arranging the blowing means of steam. The obtained combustible solid raw material can be effectively utilized as a variety of coal alternative fuels, especially the combustible solid raw material obtained by treating sewage sludge as the organic waste can be quite effectively utilized as a cement raw material and calcination fuel because the obtained solid raw material includes a large amount of clay to be used for the raw material of cement. Also, since the water treatment apparatus is provided with a membrane separation treatment apparatus, the hard decomposable COD component produced by the high temperature and pressure treatment can be removed and the soluble organic matter can be recovered.

The crushed organic waste is supplied to the preheating tank before it is supplied to the reaction tank, where it is preheated to a predetermined temperature. At this time, the spiral heat exchange agitation tube through which the heating medium is flowing in the preheating tank is swirled and the organic waste is agitated, hereby the heat efficiency of the heating medium in the preheating tank is enhanced and the scaling is prevented.

The organic waste can be agitated while heating by jetting the steam to the tangent direction of the rotating nozzle from the jetting port of the outer peripheral wall in the organic waste within the reaction tank.

The energy cost can be lowered since the quantity of heat used in the reaction tank is recovered by heat exchange with the heating medium.

The heating mediums of which each temperature is different can be obtained from a first cooler and a second cooler. By circularly using the obtained heating mediums for the suitable use at each temperature, the effective utilization of the quantity of heat can be attempted. Also, the scaling is hard to occur because the temperature of the slurried material is gradually lowered.

By adding water to the slurried material to mix with agitation in the slurry storage tank, a water soluble inorganic salt content such as a phosphorus content and a chlorine content can be eluted from the slurried material.

When the organic matter is subjected to the methane fermentation by the methane fermentation apparatus, the methane-containing gas which is effectively usable, for example, as a fuel of a boiler can be produced.

The simplification of the systemic constitution and the reduction of the equipment cost can be attempted by eliminating a heater for organic waste which was conventionally needed in the high temperature and pressure treatment. The heating temperature, treatment pressure and treatment time of the organic sludge in the high temperature and pressure treatment step can be approximately equivalent to those of the case in which the organic sludge does not contain the lump of the sludge and the admixture even when the large lump of the sludge and the admixture are present in the organic waste because the organic waste is crushed by the crusher before the high temperature and pressure treatment. Further the reaction efficiency by the uniform heating and uniform agitation of the sludge in the reaction tank can be attempted since the high temperature and pressure step comprises agitating the sludge while blowing the steam into the organic waste continuously supplied to the reaction tank and causing the reaction at a temperature of 150-250° C. and under a pressure of the steam pressure or more at this temperature for 5-120 minutes. Especially, the combustible solid raw material obtained by treating sewage sludge as the organic waste can be quite effectively utilized as a cement raw material and calcination fuel because the obtained solid raw material includes a large amount of clay to be used for the raw material of cement. Also, since the water treatment step is provided with a membrane separation treatment step, the hard decomposable COD component produced by the high temperature and pressure treatment can be removed and the soluble organic matter can be recovered.

When the organic waste is crushed to a size of 5 mm or less, the heating temperature, treatment pressure and treatment time of the organic waste in the actual high temperature and pressure treatment step can be approximately equivalent to those of the case in which the organic waste does not contain the lump of the sludge and the admixture even when the large lump of the sludge and the admixture are present in the organic waste.

Further, the crushed organic waste is supplied to the preheating tank before it is supplied into the reaction tank, where it is preheated to a predetermined temperature. At this time, the spiral heat exchange agitation tube through which the heating medium is flowing in the preheating tank is swirled and the organic waste is agitated, hereby the heat efficiency of the heating medium in the preheating tank is enhanced and the scaling is prevented.

The organic wastes can be agitated while swirling the rotation nozzle by non-driving force because the steam is jetted to the tangent direction of the rotation nozzle from the jetting port of the outer peripheral wall in the organic waste within the reaction tank.

When water is added to the slurried material to mix them with agitation, a water soluble inorganic salt content such as a phosphorus content and a chlorine content in the slurried material can be eluted from the slurried material.

When the organic matter in the separated liquid is subjected to the methane fermentation by the methane fermentation apparatus, the methane-containing gas which is effectively usable, for example, as a fuel of a boiler can be produced.

DESCRIPTION OF SIGN

Figure 1:
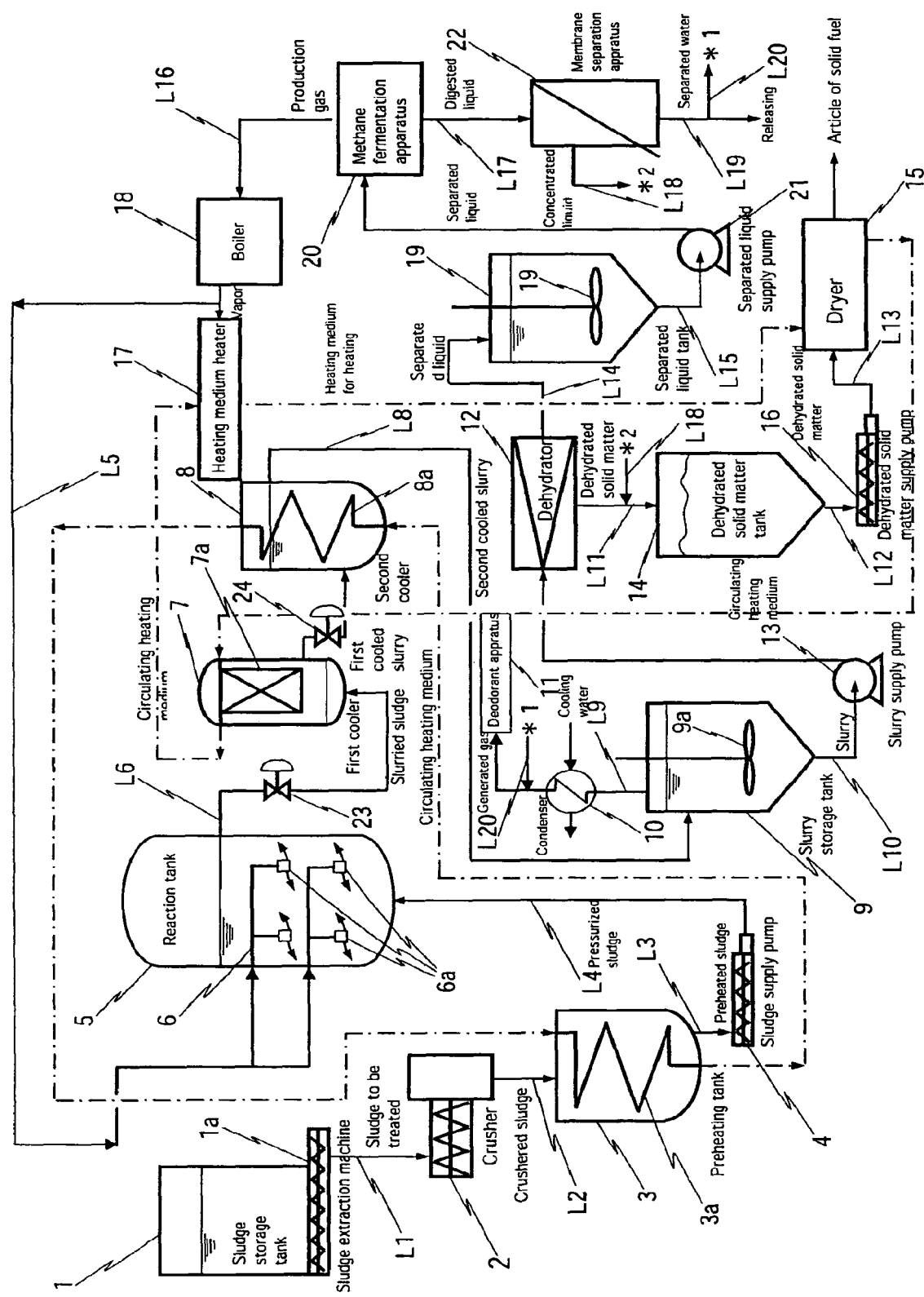
FIG. 1 Schematic flow diagram of the treatment equipment with reference to Example 1 of the present invention FIG. 2 Expanded plane view of the tangent direction jetting nozzle installed to the steam blowing means with reference to the Example 1 of the present invention

2: crusher
5: reaction tank (high temperature and pressure treatment equipment)
6: steam blowing means
6a: tangent direction jetting nozzle
9: slurry storage tank
12: dehydrator (dehydration treatment apparatus)
19: separated liquid tank (water treatment apparatus)

20: methane fermentation apparatus
22: membrane separation treatment equipment

BEST MODE FOR CARRYING OUT THE INVENTION

It is an object of the present invention to provide treatment equipment and a treatment method of the organic waste which comprises conducting the high temperature and pressure treatment to slurry it and then recovering it as a combustible solid raw material to attempt the effective utilization as a fuel, wherein the viscosity-adjusting water and energy to be used in the reaction are reduced as much as possible, thereby being capable of lowering the energy cost and the equipment cost. The object of the invention has been accomplished by the continuous reaction method which comprises charging a constant amount of the organic waste into the continuous reaction tank equipped with a steam blowing means and then blowing the steam from the steam blowing means to cause the reaction for a predetermined time while heating, pressurizing and agitating. Since the organic matter in the separated water is subjected to the methane fermentation by the methane fermentation apparatus, the methane-containing gas that is effectively usable, for example, as a fuel of a boiler can be produced. Further, the removal of hard decomposable COD component and the recovery of the soluble organic matter produced in the high temperature and pressure treatment can be conducted by installing the membrane separation treatment equipment to a part of the treatment equipment.

The embodiments of the present invention are explained based on the drawings. FIG. 1 is a schematic flow diagram for the organic sludge of one of the embodiments of the present invention.

In FIG. 1, Sign 1 is a sludge storage tank of equipment for receiving the organic waste, wherein the sludge storage tank 1 receives 70-80% by weight of the moisture content of the sludge. The sludge is organic sludge generated from the water treatment equipment to treat sewage, raw sewage and a variety of industrial waste. Sign 1a is a sludge extractor to supply the stored organic sludge to the later step apparatus in a predetermined flow rate.

Sign 2 is a crusher to crush the organic waste. Sometimes, the sludge to be treated (organic waste) forms a large lump partially and contains an admixture such as a woody material, a fibrous material and hair. The crusher 2 crushes these to a size of 5 mm or less and homogenizes the sludge.

A particulate cutting machine, a crushing pump and a homogenizer may be employed as the crusher 2. However, it is preferable that the particulate cutting machine is used because it has excellent crushing ability, homogenizing ability and treatment ability. The crusher 2 may have a constitution where a simple stage crusher is arranged or a constitution of a two-stage crusher where a pulverizer is further arranged after the crushing of a course crusher.

Sign 3 is a preheating tank and heats the crushed sludge uniformly with a heating coil 3a to 60-80° C. by circulating the circulating heating medium (90-120° C.) heated in a second cooler 8 described below through a spiral heating coil 3a swirled by a swirling motor which is not shown. In this way, since the heating coil 3a has a constitution that can be swirled, the heat efficiency of the circulation heat medium in the preheating tank 3 is enhanced and the scaling can be prevented.

Sign 4 is a sludge supply pump, and the preheated sludge heated at the preheating tank 3 is continuously supplied to the bottom of the reaction tank 5 under a pressure of 2.0-6.0 MPa·G.

The reaction tank 5 blows the steam into the pressurized sludge (organic sludge) supplied from the sludge supply pump 4, and the organic sludge is liquefied by causing the reaction with agitation at a temperature of 150-250° C. under a pressure of the steam saturation pressure or more (0.4-4.0 MPa·G) for 5-120 minutes.

Figure 2:
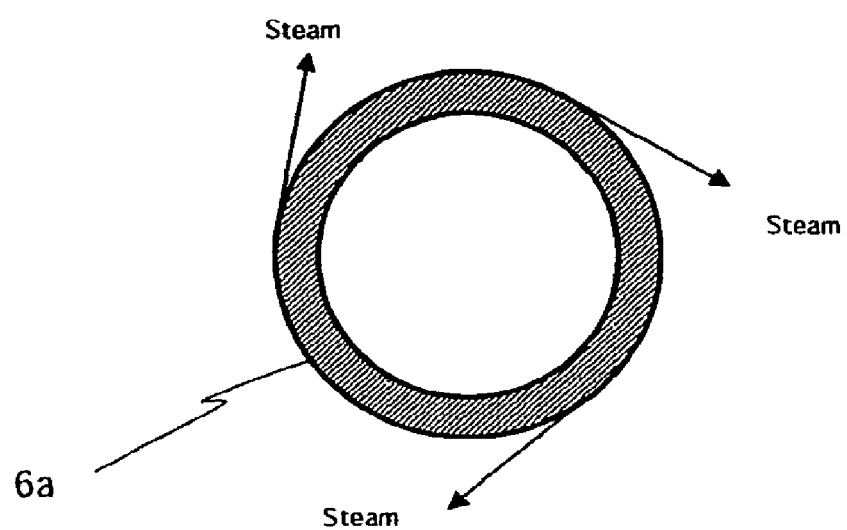

Plural stages of the steam blowing means 6 are provided at the upper part and lower part of the reaction tank 5 so that the blowing of the steam is heated and agitated uniformly as much as possible. The steam blowing means 6 has a tangent direction jetting nozzle 6a to rotate the organic sludge with agitation while jetting the steam to the tangent direction (see FIG. 2). The number of stage in which the steam blowing means 6 is arranged may be a single stage when the reaction tank 5 is a small type, and is established in dependence upon the volume of the reaction tank.

The excess steam blown for uniform heating and agitation and the gas generated by the reaction are discharged in accordance with the adjustment of the pressure of the reaction tank 5, then blown into the below-mentioned first cooler 7 and used for agitation of the liquefied sludge.

The below-mentioned coolers 7, 8 condense the steam blown into the reaction tank 5. The condensed water elutes a phosphorus content and chlorine content in the sludge. The phosphorus and chlorine content gives an adverse effect to the quality of the coal alternative fuel as a product. Accordingly, the condensed water can improve the quality of the product.

Sign 7 shows a first cooler and it adjusts the pressure within the cooler to 0.1-1.0 Mpa·G, and cools the liquefied sludge to a temperature of 120-180° C. by flash evaporation and recovers the quantity of heat of the sludge by means of the circulation medium by circulating the circulating heating medium through the cooling coil 7a.

Sign 8 is a second cooler and it adjusts the pressure within the cooler to from the atmospheric pressure to 0.1 Mpa·G, and cools the liquefied sludge to a temperature of 80-120° C. by flash evaporation and recovers the quantity of heat of the sludge by means of the circulation heating medium by circulating the circulating heating medium through the cooling coil 8a.

In the cooler 7 the outer surface of the cooling coil 7a is washed by the condensed water which is largely generated. On the other hand, in the cooler 8 the amount of the condensed water is decreased and the self-washing effect is weak, therefore, it has a structure to rotate the heating coil 8a just as the case of the preheating tank 3. Hereby, the heating efficiency of the circulating heating medium within the second cooler 8 is enhanced and the scaling can be prevented.

Sign 9 shows a slurry storage tank, and the liquefied sludge, the gas generated at the reaction tank 5 and the like are sent to the slurry storage tank 9. The generated gas is cooled by the condenser 10, and then released to atmosphere through a deodorizing device 11. The condenser 10 is washed by the purified water that is separated at the below-mentioned membrane separation apparatus 22 in order to prevent the clogging at the condenser 10 caused by the solid matter accompanied by the generated gas, and the washed water is allowed to flow into the slurry storage tank 9.

In the slurry storage tank 9 the separated liquid content from the dehydration is mixed with the liquefied sludge and purified water with agitation while rotating the agitation blade 9a.

Sign 12 is a dehydrator, and the slurried sludge sent under pressure from the bottom of the slurry storage tank 9 by a slurry supply pump 13 is separated into the solid matter and the liquid content. The moisture content of the solid matter is a degree of 45-60% by weight.

A decanter type centrifuge, screw press and belt press may be used as the dehydrator 12, however, it is preferable that the decanter type centrifuge is used.

Sign 14 shows a dehydration solid matter storage tank, where the dehydrated sludge (dehydrated solid matter) is temporarily stored.

Sign 15 shows a dryer, which heats the dehydrated solid matter sent under pressure from the bottom of the dehydrated solid matter storage tank 14 by a dehydrated solid matter supply pump 16 to evaporate the moisture content and produces a solid fuel as an article. As the heat source of the dryer 15, the circulating heating medium which was heated by the first cooler 7 and which is further heated by the heat of a boiler 18 at the heating medium heater 17 is employed. The dehydrated sludge is heated to evaporate the moisture content by supplied circulating heating medium, thereby forming the solid fuel of the article. The evaporated moisture content is sent to the combustion deodorant apparatus after the condensation by a scrubber or condenser and then released to atmosphere.

Sign 19 shows a separation liquid tank (water treatment apparatus), which stores the dehydrated separated liquid content temporarily while rotating the agitation blade 19a, and also provides the combined use of an acid fermentation apparatus as the pretreatment of the below mentioned methane fermentation apparatus 20.

Sign 20 shows the methane fermentation apparatus, which conduct the methane fermentation of the separated liquid sent under pressure from the bottom of the separation tank 19 by means of the separated liquid supply pump 21. Since the organic matter with high concentration is included in the separated liquid from the dehydrator 12, a methane-containing gas is generated from the organic matter by the methane fermentation and the effective utilization as a fuel of the boiler 18 is attempted.

The methane fermentation tank which constitutes the body of the methane fermentation apparatus 20 includes upflow anaerobic treatment apparatus (UASB TREATMENT APPARATUS), floating type methane fermentation tank and the like, however, CODcr is as high as 20,000-80,000. It is preferred that the high-speed UASB treatment apparatus is used from the viewpoint of an initial and running cost.

Sign 22 shows a membrane separation apparatus, which conducts the separation treatment of the digested liquid after the methane fermentation treatment by separation membrane. The concentrated liquid is supplied into the dehydrated solid matter storage tank 14 in the case of being possible of quality maintenance as a coal alternative fuel, however, it is treated as industrial waste when the quality is problematic. The permeated liquid is drained as the purified water and a part of it is circulated into the slurry storage tank 9 as described before.

The separation module used in the membrane separation apparatus 22 includes a tubular module, a flat plate module, a hollow fiber module and the like. As a separation membrane, RO membrane (reverse osmosis membrane), UF membrane (ultra filtration membrane), MO membrane (fine filtration membrane) NF membrane (nano-filter membrane apparatus) and the like are suitably selected, however, the nano-filter membrane or RO membrane apparatus are preferably used in dependence with the drain discharging conditions. It is preferable that the structure of the membrane separation apparatus 22 in which a plurality of flat plate modules are laminated with a space in a predetermined distance and which vibrates and rotates the modules is capable of preventing the fouling on the surface of the membrane and of lowering the numbers of the separation membranes.

In FIG. 1, sign 23 shows a first valve to adjust the flow rate of the slurried sludge supplied to the first cooler 7 from the reaction tank 5 and sign 24 shows a second valve to adjust the flow rate of the first cooling slurry supplied to the second cooler 8 from the first cooler 7. In FIG. 1, the chain line shows the circulation pass of the circulating heating medium. The circulating heating medium heated by the heating medium heater 17 returns to the heating medium heater 17 via the drying apparatus 15 and the first cooler 7. In another circulation pass of the circulating heating medium, the circulating heating medium returns to the second cooler 8 again via the preheating tank 3.

Example

Next, the method for treating the organic waste such as sewage sludge (herein after, simply referred to as sludge) using the treatment equipment of the organic waste of the above constitution will be explained with reference to the following examples.

The sludge with the moisture content of 70-85% by weight generated from the water treatment equipment is taken into the sludge storage tank 1 at a rate of 1,000 kg/hour. The received sludge is the dehydrated sludge with the moisture content of 80% by weight, combustible content (C) of 16% by weight and ash content (A) of 4% by weight obtained by the dehydrator, which is normally arranged to the water treatment equipment. However, it is not limited to the above.

The sludge extracted from the sludge storage tank 1 by the sludge extracting machine 1a is supplied to the crusher 2 via a pipeline L2. The sludge to be treated (organic sludge) is crushed to a size of 5 mm or less. Accordingly, even the sludge forms a large lump partially, and includes an admixture such as a woody material, fibrous matter and hair, the sludge is homogenized by crushing the above-mentioned material. In such a manner, the crushing and homogenization of the organic sludge is able to lower the temperature, pressure and reaction time at the subsequent reaction tank.

The crushed sludge discharged from the crusher 2 is supplied to the preheating tank 5 via the pipeline L2. Here, the heating medium (90-120° C.) heated by the second cooler 8 is circulated through the heating coil 3a which is internally arranged and the crushed sludge is heated to 60-80° C. by the heating coil 3a.

The preheated sludge heated by the preheating tank 3 is discharged via the pipeline L3 from the bottom of the reaction tank 5 and is continuously supplied to the bottom of the reaction tank 5 under a pressure of 2.0-6.0 MPa·G via the piping L 4 by the sludge supply pump 4.

In the reaction tank 5, steam is blown via the pipe line L5 into the pressurized sludge (organic sludge) supplied from the sludge supply pump 4, and the reaction was conducted at a temperature of 150-250° C. under a pressure (0.4-4.0 MPa·G) of the steam saturation pressure or more at this temperature for 5-120 minutes. Hereby, the organic sludge is liquefied and the liquefied sludge is agitated. By this agitation, the heating of the sludge is performed within ten minutes, so that the reaction temperature, the pressure and the reaction time can be decreased by the rapid temperature elevation. Also, the precipitation of the heavy content is prevented by the agitation.

The blowing of the steam at the upper and lower part of the reaction tank 5 is performed from the jetting port formed on every 120° of the outer peripheral wall through the tangent direction jetting nozzle 6a to jet the steam to the tangent direction.

The excess steam blown for uniform heating and agitation and the gas generated by the reaction is discharged upon adjusting the pressure of the reaction tank 5 and is blown into the below-mentioned first cooler 7 to be used for agitation of the liquefied sludge.

The below-mentioned coolers 7, 8 condense the steam that has been blown into the reaction tank 5. This condensed water elutes the phosphorus content and the chlorine content in the sludge. The phosphorus and chlorine content would give an adverse effect to the quality of the coal alternative fuel as a product. Thus, the condensed water enables the product to improve the quality. The sludge with the moisture content of 89.71% by weight at the exit of the reaction tank 5 is sent under pressure of 1,252 kg/h. The sludge composition has the combustible content (C) of 7.09% by weight and the ash content (A) of 3.19% by weight.

After that, the slurried sludge is supplied to the first cooler 7 from the proximity of the liquid surface of the reaction tank 5 via the pipeline L6 in which the first valve 23 is opened. Here, the pressure within the cooler is adjusted to 0.1-1.0 MPa, the liquefied sludge is cooled to a temperature of 120-180° C. by flash evaporation by circulating the circulating heating medium through the cooling coil 7a to recover the quantity of heat.

The first cooled slurry that passed through the first cooler 7 is supplied to the second cooler 8 via the pipeline L7 of which the first valve 24 is opened. Here, the pressure within the cooler is adjusted to from the atmospheric pressure to 0.1 MPa·G. Then, the first cooled slurry is cooled to a temperature of 80-120° C. by the flash evaporation and the circulating heating medium is circulated through the cooling coil 8a to recover the quantity of heat of the sludge by the circulating heating medium. The sludge composition at the exit of the cooler 8 has the moisture content of 90.53% by weight, the combustible content (C) of 6.53% by weight and the ash content (A) of 2.94% by weight.

The second cooled slurry that passed through the second cooler 8 and the gas generated at the reaction tank 5 is supplied to the slurry storage tank 9 via the pipeline L 8. The gas generated here is cooled by the condenser 10 via the pipeline 9 and then is released to atmosphere via the deodorant apparatus 11. The condenser 10 is washed by the purified water which is separated at the below-mentioned membrane separation apparatus 22 in order to prevent the clogging at the condenser 10 caused by the solid matter accompanied by the generated gas. And the washed water is allowed to flow into the slurry storage tank 9.

In the slurry storage tank 9, the separate liquid content from the dehydration is mixed with the liquefied sludge and the purified water with agitation while rotating the agitation blade 9a. Accordingly, the water-soluble organic salt content such as phosphorus content and chlorine content is eluted. This procedure is performed in order to enhance the quality of the solid fuel. The amount of the purified water is adjusted in dependence with the concentration of phosphorus, chlorine and the like. The sludge composition at the exit of the slurry storage tank 9 includes the moisture content of 90.24% by weight, the combustible content (C) of 6.73% by weight and the ash content (A) of 3.03% by weight.

The slurried sludge discharged from the bottom of the slurry storage tank 9 via the pipeline L10, is sent under pressure to the dehydrator apparatus 12 by the slurry supply pump 13. Here, the slurried sludge is separated into the solid matter and the liquid content. The moisture content of the solid matter is a degree of 45-60% by weight.

The dehydrated sludge dehydrated by the dehydrator apparatus 12 (dehydrated solid matter) is temporally stored at the dehydrated solid matter storage tank 14 via the pipeline L 11. After that, the hydrated solid matter is passed through the pipeline 12 and sent under pressure to the dryer 15 via the pipeline L 13 from the lower part of the dehydration solid matter storage tank 14 by the dehydration solid matter supply pump 16. The sludge composition at the exit of the dehydrator 12 includes the moisture content of 60% by weight, the combustible content (C) of 27.58% by weight and the ash content (A) of 12.42% by weight.

In the dryer 15, the dehydrated solid matter is heated to evaporate the moisture and the article of the solid matter is prepared. As the heat source of the dryer 15, the circulating heating medium which was heated by the first cooler 7 and which is further heated by the heat of a boiler 18 at the heating medium heater 17 is employed. The dehydrated sludge is heated to evaporate the moisture content by supplied circulating heating medium, thereby forming the solid fuel of the article. The evaporated moisture content is sent to the combustion deodorant apparatus after the condensation by a scrubber or condenser and then released to atmosphere. The sludge with the moisture content of 10% by weight at the exit of the dryer 15 is sent under a pressure of 133 kg/hour. The sludge composition here includes the combustible content (C) of 63.08% by weight and the ash content (A) of 26.92% by weight.

The separated liquid separated from the dehydrator 12 is supplied to the separated liquid tank 19 via the pipeline L 14. The separated liquid content from the dehydration is temporarily stored while rotating the agitation blade 19a. The separated liquid tank 19 is used in combination with the acid fermentation apparatus as the pretreatment of the methane fermentation apparatus 20.

The separated liquid withdrawn from the bottom of the separated liquid tank 19 via the pipeline L 15 by the separated liquid supply pump 21 is supplied to the methane fermentation apparatus 20. Here, the separated liquid is subjected to the methane fermentation. The organic matter with high concentration is included in the separated liquid from the dehydrator 12. Therefore, the methane-containing gas is produced from the organic matter by the methane fermentation and is effectively utilized as a fuel of the boiler 18 via the pipeline L 16. The amount of fuel to be used is improved in 27.6% calculated by formula (1): (68.2−18.8)/68.2=0.724.

The digestion liquid after the methane fermentation treatment is supplied to the membrane separation apparatus 22 via the pipeline 17. The digestion liquid is subjected to the separation treatment by the separation membrane and is supplied to the dehydration solid matter storage tank 14 via the pipeline L 18 when the quality maintenance as a coal alternative fuel is possible. However, when there are problems on the quality, the concentrated liquid is treated as industrial waste. The permeated liquid through the separation membrane is drained as the purified water via the pipeline L 19, and the part of them is circulated to the slurry storage tank 9 via the pipeline L 20 as described above.

Industrial Applicability

The present invention is useful for treatment equipment of organic waste that is capable of recovering the organic waste such as raw sewage and industrial waste treatment sludge as a cement raw material, a calcination fuel, a coal alternative fuel and the like.

The invention claimed is:
1. A system for treating an organic waste comprising:
a preheating tank to preheat the organic waste, wherein the preheating tank includes a spiral heat exchange agitation tube to agitate the organic waste supplied into the preheating tank while preheating with heat of a heating medium by flowing the heating medium through the tube and swirling the tube;

a pump to pressurize the organic waste;

a high temperature and pressure treatment apparatus following the preheating tank and the pump, the organic waste being supplied to the high temperature and pressure treatment apparatus under pressure from the pump, the high temperature and pressure treatment apparatus producing a slurried material by treating the pressurized organic waste from the pump at a high temperature and a high pressure;

a steam blowing means to blow steam into the organic waste in the high temperature and pressure treatment apparatus;

wherein the high temperature and pressure treatment apparatus is formed as a continuous reaction tank to which the pressurized organic waste is continuously supplied from the pump and to which the steam is blown from the steam blowing means to cause a reaction while heating, pressurizing and agitating;

a dehydration treatment apparatus following the high temperature and pressure treatment apparatus to dehydrate the slurried material from the high temperature and pressure treatment apparatus, the dehydration treatment apparatus producing a separated liquid product and a separated solid product, the separated solid product from the dehydration treatment apparatus comprising a sufficient combustible content to produce a fuel product from the separated solid product; and a water treatment apparatus following the dehydration treatment apparatus to treat the separated liquid product from the dehydration treatment apparatus.

2. The system of claim 1, wherein the steam blowing means has a tangent direction jetting nozzle formed in an outer peripheral wall of the steam blowing means, the jetting nozzle jetting steam from the jetting nozzle in the tangent direction relative to the outer peripheral wall of the steam blowing means to rotate the organic waste in the high temperature and pressure treatment apparatus with agitation.

3. A system for treating an organic waste comprising:

a pump to pressurize the organic waste;

a high temperature and pressure treatment apparatus following the pump, the organic waste being supplied to the high temperature and pressure treatment apparatus under pressure from the pump, the high temperature and pressure treatment apparatus producing a slurried material by treating the pressurized organic waste from the pump at a high temperature and a high pressure;

a steam blowing means located in the high temperature and pressure treatment apparatus, at least one jetting nozzle being formed in an outer peripheral wall of the steam blowing means to blow steam outwardly from the outer peripheral wall of steam blowing means and into the organic waste in the high temperature and pressure treatment apparatus;

wherein the high temperature and pressure treatment apparatus is formed as a continuous reaction tank to which the pressurized organic waste is continuously supplied from the pump and to which the steam is blown from the steam blowing means to cause a reaction while heating, pressurizing and agitating;

a depressurization apparatus following the high temperature and pressure treatment apparatus, the depressurization apparatus producing a depressurized slurried material;

a dehydration treatment apparatus following the depressurization apparatus, the dehydration treatment apparatus comprising a solid-liquid separator that is operable to perform an initial separation of liquid material from the depressurized slurried material, the solid-liquid separator dividing the depressurized slurried material into a separated liquid output and a separated solid output having an ash content and a sufficient combustible content to produce a fuel product from the separated solid output; and a water treatment apparatus following the dehydration treatment apparatus to treat the separated liquid output from the dehydration treatment apparatus.

4. The system of claim 3, wherein the depressurization apparatus comprises a first cooler following the high temperature and pressure treatment apparatus to flash and cool the slurried material from the high temperature and pressure treatment apparatus and a second cooler following the first cooler to flash and further cool the slurried material cooled by the first cooler.

5. The system of claim 4, further comprising a heat recovery apparatus to recover a quantity of heat released from the slurried material in at least one of the first and second coolers.

6. The system of claim 3, further comprising a slurry storage tank following the high temperature and pressure treatment apparatus to store the slurried material, the slurry storage tank including a water inlet to add water to the slurried material and an agitator for mixing the slurried material and the water with agitation.

7. The system of claim 3, wherein the water treatment apparatus includes a methane fermentation apparatus to digest organic material in the separated liquid output to thereby produce a methane-containing gas.

8. The system of claim 3, further comprising a crusher preceding the high temperature and pressure treatment apparatus to crush the organic waste before providing the organic waste to the high temperature and pressure treatment apparatus.

9. The system of claim 3, wherein the pump pressurizes the organic waste to a pressure of 2.0-6.0 MPa·G before providing the pressurized organic waste to the high temperature and pressure treatment apparatus.

10. The system of claim 3, wherein the high temperature in the high temperature and pressure treatment apparatus is 150-250° C.

11. The system of claim 3, wherein the high pressure in the high temperature and pressure treatment apparatus is at or above the steam saturation pressure at the high temperature.

12. The system of claim 3, wherein the high pressure in the high temperature and pressure treatment apparatus is 0.4-4.0 MPa·G.

13. The system of claim 3, further comprising a dryer following the dehydration treatment apparatus to dry the separated solid output from the dehydration treatment apparatus, the dryer producing a solid fuel product from the separated solid output.

14. The system of claim 3, wherein the water treatment apparatus includes a membrane separation treatment apparatus to recover a residual solid matter from the separated liquid output as a condensed liquid.

15. The system of claim 3, wherein the separated solid output from the dehydration treatment apparatus comprises at least one of a combustible content over 20% by weight and a moisture content of 45-60% by weight.

16. The system of claim 13, wherein the solid fuel output from the dryer comprises at least one of a combustible content over 60% by weight and a moisture content of 10% by weight.

17. The system of claim 3, wherein excess steam from the high temperature and pressure treatment apparatus is blown into a first cooler following the high temperature and pressure treatment apparatus.

18. The system of claim 7, wherein the methane-containing gas from the methane fermentation apparatus is directed as fuel to a boiler, the boiler producing steam for the steam blowing means of the high temperature and pressure treatment apparatus.

19. A system for treating an organic waste comprising:
a pump to pressurize the organic waste;
a high temperature and pressure treatment apparatus following the pump, the organic waste being supplied to the high temperature and pressure treatment apparatus under pressure from the pump, the high temperature and pressure treatment apparatus producing a slurried material by treating the pressurized organic waste from the pump at a high temperature and a high pressure;
a steam blowing means located in the high temperature and pressure treatment apparatus, at least one jetting nozzle being formed in an outer peripheral wall of the steam blowing means to blow steam outwardly from the outer peripheral wall of the steam blowing means and into the organic waste in the high temperature and pressure treatment apparatus;
wherein the high temperature and pressure treatment apparatus is formed as a continuous reaction tank to which the pressurized organic waste is continuously supplied from the pump and to which the steam is blown from the steam blowing means to cause a reaction while heating, pressurizing and agitating;
a dehydration treatment apparatus following the high temperature and pressure treatment apparatus to dehydrate the slurried material from the high temperature and pressure treatment apparatus, the dehydration treatment apparatus producing a separated liquid product and a separated solid product, the separated solid product from the dehydration treatment apparatus comprising a sufficient combustible content to produce a fuel product from the separated solid product; and
a water treatment apparatus following the dehydration treatment apparatus to treat the separated liquid product from the dehydration treatment apparatus.

20. The system of claim 19, wherein the at least one jetting nozzle blows the steam in a tangent direction relative to the outer peripheral wall of the steam blowing means to rotate the organic waste in the high temperature and pressure treatment apparatus.

* * * * *

UNITED STATES PATENT AND TRADEMARK OFFICE
CERTIFICATE OF CORRECTION

| | |
|---|---|
| PATENT NO. | : 8,043,505 B2 |
| APPLICATION NO. | : 11/919276 |
| DATED | : October 25, 2011 |
| INVENTOR(S) | : Akiteru Noguchi et al. |

It is certified that error appears in the above-identified patent and that said Letters Patent is hereby corrected as shown below:

Title Page, above Item (65), insert:

--(30) Foreign Application Priority Data

27 April 2005   (JP).........................2005-129942--

Signed and Sealed this
Third Day of January, 2012

David J. Kappos
*Director of the United States Patent and Trademark Office*